United States Patent
Ji et al.

(10) Patent No.: US 6,887,702 B2
(45) Date of Patent: May 3, 2005

(54) PLASMID ORIGINATED FROM BIFIDOBACTERIUM, RECOMBINANT EXPRESSION VECTOR USING THE PLASMID AND TRANSFORMATION METHOD

(75) Inventors: Geun-Eog Ji, Seoul (KR); Myeong-Soo Park, Seoul (KR); Yun-Hee Kang, Seoul (KR); Jung-Min Seo, Seoul (KR)

(73) Assignee: Bifido Co., Ltd., Seoul (KR)

( * ) Notice: Subject to any disclaimer, the term of this patent is extended or adjusted under 35 U.S.C. 154(b) by 92 days.

(21) Appl. No.: 10/258,440

(22) PCT Filed: Mar. 30, 2001

(86) PCT No.: PCT/KR01/00527

§ 371 (c)(1),
(2), (4) Date: Oct. 24, 2002

(87) PCT Pub. No.: WO02/068662

PCT Pub. Date: Sep. 6, 2002

(65) Prior Publication Data

US 2004/0014221 A1 Jan. 22, 2004

(30) Foreign Application Priority Data

Feb. 24, 2001 (KR) .................................... 2001-0009526

(51) Int. Cl.[7] ............................. C12N 15/74; C12N 1/21
(52) U.S. Cl. ................................. 435/320.1; 435/252.3; 435/476
(58) Field of Search .................. 435/320.1, 252.3, 435/476, 471

(56) References Cited

PUBLICATIONS

Missich et al., "Transformation of *Bifidobacterium longum* with pRM2, a Constructed *Escherichia coli—B. longum* Shuttle Vector", Plasmid, 32, 208–211 (1994).*

Park et al., "Sequence analysis of plasmid pKJ50 from *Bifidobacterium longum*", Microbiology 145:585–592 (1999).*

Genbank Accession No. NC_002635 (Ji, G.E., Park, M.S., and Shin, D.W.) Jan. 2, 2001.

Joon–Seok Song et al., "Characterization of the Replication Region of *Enterococcus faecalis* Plasmid p703/5," J. Microbiol. Biotechnol., 1999, (9)1, 91–97.

Sambrook et al., Molecular Cloning, Plasmid Vectors p. 1.13, Second Edition.

Park et al., "Sequence Analysis of Plasmid pK150 from *Bifidobacterium Longum*," Microbiology, vol. 145, pp. 585–592, 1999.

* cited by examiner

*Primary Examiner*—James Ketter
*Assistant Examiner*—Nancy T. Vogel
(74) *Attorney, Agent, or Firm*—Foley & Lardner, LLP

(57) ABSTRACT

The present invention relates to a new plasmid originated from (*Bifidobacterium*) a recombinant expression vector and transformation method using the same. More particularly, the present invention relates to a plasmid pMG1 having nucleotide sequence represented by SEQ.ID.NO.1; (*Bifidobacterium longum*) MG1 including the plasmid pMG1; and a shuttle vector which can be replicated in both (*Bifidobacterium*) and (*E. coli*), and comprises (Mob) gene having nucleotide sequence represented by SEQ.ID.NO.2. (Rep) gene having nucleotide sequence represented by SEQ.ID.NO.3 and a selection marker. The shuttle vector and the promoter of the present invention can be used for expressing target gene without additional purification process. The protein expressed from the target gene in (*Bifidobacterium*) can be added to food, therefore, the protein can be used for preparing food additives or oral vaccine, Furthermore, the potential and the possibilty of probiotics using (*Bifidobacterium*) can promoted through the development of the shuttle vector.

13 Claims, 6 Drawing Sheets

PLASMID ORIGINATED FROM BIFIDOBACTERIUM, RECOMBINANT EXPRESSION VECTOR USING THE PLASMID AND TRANSFORMATION METHOD

TECHNICAL FIELD

The present invention relates to a new plasmid originated from *Bifidobacterium*, a recombinant expression vector and a transformation method using the same. More particularly, the present invention relates to a plasmid pMG1 having a nucleotide sequence represented by SEQ ID NO: 1; *Bifidobacterium longum* MG1 containing the plasmid; and a shuttle vector that is replicated in both *Bifidobacterium* and *E. coli* and comprises a Mob gene having a nucleotide sequence represented by SEQ ID NO: 2, a Rep gene having a nucleotide sequence represented by SEQ ID NO: 3 and a selection marker.

BACKGROUND ART

Human intestines contain various microorganisms propagating therein, composing normal intestinal flora. Composition and activity of such intestinal flora may widely influence nutrition, bio-functionality, drug efficiency, carcinogenesis, aging, immune responses, resistance to infection, and the body's responses to other stresses as well as heath of animal and human, in positive manners. The intestinal flora comprises more than 500 different species. A relatively small number of bacteria reside in the stomach and the upper part of the small intestine, while increasing in number in the large intestine. As described above, the intestinal flora offers positive effects on human health. It is known that *Bifidobacterium* sp. in normal intestinal flora is of high importance. Such a fact can be inferred by observing that *Bifidobacterium* sp. inhabits the large intestine of humans, throughout their entire lives. Also, it was revealed that breast-fed infants have a larger number of *Bifidobacterium* sp. than bottle-fed infants, leading to the breast-fed infants having a lower occurrence of diarrhea. However, it is known that the number of *Bifidobacterium* sp. is rapidly decreased with aging.

Distribution of the normal intestinal flora in humans changes depending on diverse factors such as age, race, living environments, diet, etc. The diet especially may have big effects on the normal intestinal flora. Reportedly, people living a healthy long life or people with low incidence of adult diseases have a large number of intestinal *Lactobacillus,* compared to other people, For this reason, the importance of selecting foods to elevate well-balanced distribution of the intestinal flora is rising. With an aim of obtaining well-balanced distribution of the intestinal flora by ingesting *Lactobacillus* strains, active studies for development of food products prepared by adding *Lactobacillus* to conventional dairy products, including yogurts, are underway.

Thus, there have been many attempts to use *Lactobacillus* in producing health foods and medicaments, as interest in personal health is rising. Actually, various foods and medicaments comprising *Lactobacillus* have been developed. The *Lactobacillus* strains, which are currently used in Korea, are all developed in foreign countries, so there may be differences in their characteristics from strains residing in the intestines of Korean people. It is expected that the *Lactobacillus* strains residing in the intestines of only Korean people may exhibit higher physiological activities, due to their greater adaptability to the Korean people, than those of any other *Lactobacillus* strains developed up to now. Accordingly, attempts for development of novel foods and medicaments comprising *Lactobacillus* strains which are fit to Korean people, by isolating useful Korean-type *Lactobacillus* strains from Korean people, have been made.

*Bifidobacterium* sp. is Gram-positive and Y-shaped or V-shaped. It is nonmotile, anaerobic, nonsporing, and fermenting. *Bifidobacterium* sp. is traditionally categorized as lactic acid bacteria. Fermentation by *Bifidobacterium* sp. leads to production of acetate and lactate as main products, at a ratio of 3:2. The GC content of its DNA is 55 to 64%. *Bifidobacterium* sp. is known to be host-specific. In humans, *B. bifidum, B. longum, B. breve, B. infantis*, and *B. adolescentis* are found. The above five species have been used as probiotics. Probiotics refers to microorganisms as nutrients which exhibit beneficial effects on their hosts by maintaining desirable balance of intestinal microbes and enhancing physiological characteristics thereof (Fuller, R., *Journal of Applied Bacteriology*, 66: 365–378, 1989).

To date, many vector systems derived from *Lactobacillus* sp. and *Lactococcus* sp., both being categorized as lactic acid bacteria, have been developed. It is expected that commercialization of such vector systems based on technologies of gene modification is realizable. Development of vector systems derived from *Bifidobacterium* sp., which is better suited to the intestines, is still in initial stages. Plasmids derived from *Bifidobacterium* strains so far studied are described below.

In the early research, it was believed that only *B. longum* among bacteria isolated from humans carries a plasmid. The plasmid isolated from the *B. longum* was ligated with a vector for transformation, derived from *E. coli* thus developing a shuttle vector. It was reported that plasmids exist in *B. globosum, B. asteroides*, and *B. indicum*. The plasmids are grouped according to their genetic homology, as determined by electrophoresis patterns or Southern hybridization. It was also reported that another strain, *B. breve* has a plasmid (Sgorbati, B. et al, *Microbiologica.*, 6: 169–173, 1983; Tannock, G. W. et al., *J. Clin. Microbiol.*, 28: 1225–1228, 1990).

Vectors using plasmids of *Bifidobacterium* strains were rarely reported until the 1990s. *B. longum* B2577 harbors a plasmid pMB1 1.9 kb long. The pMB1 was cloned into an *E. coli*-derived vector, and a cleavage map thereof was generated. In 1994, a shuttle vector pRM2 that is replicated in *E. coli* and *B. longum* was developed using pMB1 as a basic vector, and transformation of *B. longum* via electroporation was achieved. Recently, the entire nucleotide sequence of pMB1 was determined (Mateuzzi, D., et al., *Letters in Applied Microbiology*, 11:220–223, 1990; Missichi, R., et al, *Plasmid,*32:208–211, 1994; Argnami, A. et al., *Microbiology,* 142:109–114, 1996). The *Bifidobacterium* sp. has a thick multi-layered cell wall. The cell wall contains diverse components such as peptidoglycan, polysaccharide, lipoteichoic acid and protein. Such characteristics of the cell wall contribute to its role as a barrier against intake of foreign DNA molecules. For the purpose of transforming *Bifidobacterium* sp., although various attempts have been made in terms of academic or industrial applications, only few successes have been achieved. There was a report in which *B. longum* was employed to construct a transformant through low efficiency electroporation (Missich, R et al., *Plasmid,*32:208–211, 1994).

Using the plasmid pMB1 isolated above, a shuttle vector pNC7 was constructed, and a transformation method for application in various species of *Bifidobacterium* sp. was developed. The transformation efficiency varied between $1.0 \times 10^1$ to $1.2 \times 10^5$ CFU/μg DNA, according to species. According to the method, Actilight®P was used as a glucose source in a medium, and the bacteria in log-growth phase were collected, preparing competent cells. The conditions for electroporation were set to 12.5 kV/cm, 100 Ω, 25 μF to perform transformation. In Japan, a shuttle vector which is replicated in E. coli and Bifidobacterium sp. was developed using a 3.6 kb plasmid (pTB6) isolated from B. longum (see Table 1) (Matsummura, H. et al., Biosci. biotech. Biochem., 61(7):1211–1212, 1997).

Meanwhile, Korean researchers first isolated plasmids from Bifidobacterium strains in 1994, and the plasmids were divided into several homology groups based on results of Southern hybridization (Hyun-Seo Jung et al., presented at the Spring Conference of the Korean Society of Food Science and Technology, 1994; Joo-Hun Lee et al., presented at the Spring Conference of the Korean Society of Food Science and Technology, 1997). Among those strains, two strains exhibited relatively strong resistance to erythromycin and tetracycline. Such resistance of the strains was considerably reduced upon loss of those plasmids. Another strain B. longum KJ harbors two distinct plasmids pKJ36 and pKJ50 (see Table 1). Each of these plasmids was cloned into an E. coli-derived vector for transformation, thereby generating cleavage maps thereof. Those entire nucleotide sequences were found, compared and analyzed (Myoung-Soo, Park et al., presented at the Fall Conference of the Korean Society for Applied Microbiology, 1995; 1996; 1997). Results showed that the two plasmids have very similar characteristics, and each contains an ORF which shares significant amino acid homology with Rep and Mob proteins expressed from certain plasmids in Gram-positive and Gram-negative bacteria. Each ORF was expressed at translation/transcription levels. Based on those results, shuttle vectors pBKJ50F, pBKJ50R and pBRepA which replicate in E. coli and Bifidobacterium sp. were constructed to use in transforming Bifidobacterium sp.

As described above, all the vectors developed by using the Bifidobacterium—derived plasmids contain a foreign antibiotic resistance gene as a selection marker. It is a shortcoming that they cannot be applied directly for foods. Therefore, there is a need for development of a food-grade vector which can be used for food in a safe manner. Development for new shuttle vectors is ongoing in such manners that antibiotic resistance genes are removed for replacement with a food-grade selection marker, and promoter/operator sequences are inserted to regulate foreign gene expression. Table 1 shows plasmids in Bifidobacterium sp. and shuttle vectors derived therefrom.

TABLE 1

| Plasmid (kb in size) | Host cell | Vector | Selection marker |
|---|---|---|---|
| pMB1(1.9) | B. longum | pRM2 | Spectinomycin[a] Ampicillin[b] |
| | | pNC7 | Chloramphenicol[a] Ampicillin[b] |
| pKJ36(3.6) | B. longum KJ | pEKJ36 | Chloramphenicol[a] Ampicillin[b] |
| pKJ50(5.0) | B. longum KJ | pBKJ50F pBKJ50R pBRepA | Chloramphenicol[a,b] Chloramphenicol[a,b] |
| pNBb1(5.6) | B. breve | Not developed | |
| pTB6(3.6) | B. longum | pBLES100 | Streptomycin[a] Ampicillin[b] |

Note:
[a]selection marker expressed in Bifidobacterium sp.
[b]selection marker expressed in E. coli In view of the above problems, the inventors have made an effort to develop a shuttle vector which is replicated in both E. coli and Bifidobacterium sp. and express a target gene, thereby capable of being used as a food additive and for preparing oral vaccines without the need for purification upon expression of the target gene in Bifidobacterium sp., and a promoter which directs a strong expression of the target gene in Bifidobacterium sp.

DISCLOSURE OF THE INVENTION

Thus, the present invention provides a plasmid pMG1 having a nucleotide sequence represented by SEQ ID NO: 1 and a Bifidobacterium longum MG1 containing the plasmid.

Another object of the invention can be accomplished by the provision of a shuttle vector which is replicated in both Bifidobacterium sp. and E. coli and comprises a Mob gene having a nucleotide sequence represented by SEQ ID NO: 2, a Rep gene having a nucleotide sequence represented by SEQ ID NO: 3 and a selection marker.

Preferably, the shuttle vectors may be constructed using a plasmid pMG1 and an E. coli-derived vector for transformation. The E. coli-derived vector for transformation is any one selected from the group consisting of pEK104 (provided by Prof. Hyou-II Chang, Genetic Biochemistry Lab. in The University of Korea Graduate School of Biotechnology), pUC19 (Clontech) and pBR322 (Clontech). Particularly, the invention provides a shuttle vector pBES2 constructed using pMG1 and pEK104.

As for the shuttle vectors according to the invention, it is preferable that the selection marker is at least one selected from the group consisting of an ampicillin resistance gene, a kanamycin resistance gene and a chloramphenicol acetyl transferase (CAT) gene.

Another object of the invention can be accomplished by the provision of a recombinant vector in which a target gene encoding a target protein is inserted into a shuttle vector pBES2.

Another object of the invention can be accomplished by the provision of a transformation method comprising the steps of, (a) constructing a shuttle vector that is replicated in both Bifidobacterium sp. and E.coli using the plasmid derived from Bifidobacterium sp. and that derived from E. coli;

(b) constructing a recombinant vector by inserting a target gene encoding a target protein into the shuttle vector; and (c) transforming the Bifidobacterium sp. used in the step (a) with the recombinant vector constructed in the step (b).

Yet another object of the invention can be accomplished by the provision of a promoter of Bifidobacterium sp. GE65 having a nucleotide sequence represented by SEQ ID NO: 4 or SEQ ID NO: 5.

Hereinafter, the invention is described in detail.

First, the invention is directed to a plasmid pMG1 having a nucleotide sequence represented by SEQ ID NO: 1 and a B. longum MG1 containing the plasmid, To isolate a novel Bifidobacterium strain inhabiting in the large intestines of Korean people, the present inventors isolated a novel plasmid and a strain from human feces, according to a known method for isolating Bifidobacterium strains.

Bifidobacterium sp. is known to be host-specific. In humans, B. bifidum, B. longum, B. breve, B. infantis, and B. adolescentis are found. The inventors isolated a novel strain of B. longum which has never been found so far in human feces, and isolated a novel plasmid therefrom. The inventors named the novel strain of *B. longum* as *Bifidobacterium longum* MG1 and the novel plasmid as pMG1. The strain of *B. longum* MG1 containing the plasmid pMG1 was deposited in an international depository authority, the Korean Culture Center of Microorganisms (KCCM), located at 361-221. Yurim B/D. Hongie-1-dong, Seodaemun-gu, Seoul 120-091, Republic of Korea, under deposit No. KCCM-10254 on Mar. 28, 2001.

The *B. longum* MG1 isolated in the invention is identified by performing Gram staining, and an analysis of F6PPK (fructose-6-phosphate phosphoketolase) which is a unique enzyme of *Bifidus* strain. The results showed that above strain is morphologically claviform and Y-shaped. As revealed in Gram staining, the strain is Gram positive. It exhibited the F6PPK activity, demonstrating a *Bifidus* strain.

The plasmid pMG1 isolated in the invention is 3,682 bp long with a G+C content of 65.1%. Sequence analysis using DNASIS (Hitachi) revealed that the plasmid contains several ORFs (open reading frames) that are expected to be expressed. Among those ORFS, two sequences which share high homology at their amino acid levels with other proteins were named ORF I and ORF II, respectively. ORF I protein has a molecular weight of 29,000 Da and shows high homology with replication proteins of diverse Gram negative or Gram positive bacteria. In addition, ORF I comprises nucleotide sequences known as iteron, in which a 22 bp unit is repeated 4 times upstream thereof. On the other band, ORF II protein has a molecular weight of 71,000 Da and shows high amino acid homology with mobilization proteins of other bacteria. There is a nucleotide sequence of ori-T upstream of the ORF II, which is presumed to play an important role in bacterial conjugation. Moreover, each ORF has an AGGA sequence 10 to 15 bp upstream thereof, which is expected to be a ribosome-binding site. ORF I has iteron sequences in its genetic structure in which a nucleotide sequence of 22 bp appears repeatedly 4 times upstream thereof. It is known that such iteron sequences are involved in regulating replication of plasmids. Also, it is known that the ori-T sequence located upstream of the ORF II, the sequence being 12 bp long, is an origin at which plasmid transfer occurs via conjugation.

The invention is also directed to a shuttle vector which is replicated in both *Bifidobacterium* sp. and *E. coli* and comprises a Mob gene having a nucleotide sequence represented by SEQ ID NO: 2, a Rep gene having a nucleotide sequence represented by SEQ ID NO: 3 and a selection marker.

Conventionally, when a target protein is expressed in *E. coli* which has been mainly used as a host cell for transformation, there is a need for an additional purification step to eliminate toxicity of the proteins expressed in *E. coli*. Accordingly, research has been underway to try use *Bifidobacterium* sp. that exhibits no toxicity to humans as a host cell. In addition, all conventional vectors which have been developed so far by using *Bifidobacterium*-derived plasmid, contain a foreign antibiotic resistance gene as a selection marker. This is a shortcoming, in that they cannot be applied directly for foods.

The invention is directed to a food-grade vector which can be applied for food in a safe manner to overcome such above problems.

Specially, the invention is directed to a shuttle vector pBES2 which is replicated in both *Bifidobacterium* sp. and *E. coli* and comprises a Mob gene having a nucleotide sequence represented by SEQ ID NO: 2, a Rep gene having a nucleotide sequence represented by SEQ ID NO: 3, and a selection marker. FIG. 2 schematically illustrates a cleavage map of the shuttle vector pBES2 and a construction process thereof. The shuttle vector pBES2 according to the invention showed high stability, maintaining its integrity within the cell even after 30 cycles of cell division.

The shuttle vector pBES2 according to the invention may be constructed by using a plasmid pMG1 and an *E. coli*-derived vector for transformation. The *E. coli*-derived vector for transformation is any one selected from the group consisting of pEK104, pUC19 and pBR322. Specially, the invention constructed a shuttle vector pBES2 using plasmids pMG1 and pEK104.

It is preferable that the selection marker contained in the shuttle vector is at least one selected from the group consisting of an ampicillin resistance gene, a kanamycin resistance gene and a chloramphenicol acetyl transferase gene. Specially, the selection markers used herein are lie ampicillin resistance gene and chloramphenicol acetyl transferase gene.

The invention is directed to a recombinant vector in which a target gene encoding a target protein was inserted into a shuttle vector pBES2.

Preferably, the target gene may be any one selected from the group consisting of an amylase gene, a gene for vaccine, a gene for anticancer treatment, and a gene exhibiting various physiological activities. Specially, constructed herein is a recombinant vector pYBamy59 in which an amylase gene as the target gene has been inserted into the shuttle vector pBES2. The recombinant vector pYBamy59 is 10.1 kb long. FIG. 3 schematically illustrates a cleavage map of the recombinant vector pYBamy59 and a construction process thereof.

The invention is directed to a new transformation method. According to the method, a *Bifidobacterium* strain, whose plasmid is used to construct a shuttle vector, is transformed with a recombinant vector carrying a target gene inserted into the shuttle vector, thus obtaining a transformant. The transformant can express the target gene at high efficiency. A detailed description of the method is as follows.

First, a shuttle vector is constructed using a *Bifidobacterium*-derived plasmid and *E. coli*-derived plasmid, the shuttle vector being capable of replicating in both *Bifidobacterium* sp. and *E. coli*. The shuttle vector is then ligated with a target gene encoding a target protein, constructing a recombinant vector. The method for constructing the recombinant vector may be a commonly known method.

As a host cell for transforming with the recombinant vector, the invention specially used a *Bifidobacterium* strain that is used to construct the shuttle vector.

The transformation efficiency can be considerably improved by using the original *Bifidobacterium* strain from which a shuttle vector is prepared, the shuttle vector being used to construct a recombinant vector, as a host cell for transformation. Specially, the invention prepared competent cells for transformation with *Bifidobacterium* sp. and constructed a recombinant vector with the shuttle vector, which was derived from the same *Bifidobacterium* sp. as such competent cells. In addition, the transformation efficiency could be increased more than 10 times by oxyrase treatment.

The *B. longum* MG1, which was transformed with the recombinant vector pYBamy59, was deposited in an international depository authority, the Korean Culture Center of Microorganisms (KCCM), located at 361-221, Yurim B/D, Hongie-1-dong, Seodaemun-gu, Seoul 120-091, Republic of Korea, under deposit No. KCCM-10255 on Mar. 28, 2001.

The invention is directed to a promoter of *Bifidobacterium* sp. GE65 having a nucleotide sequence represented by SEQ ID NO: 4 or SEQ ID NO: 5. To increase expression efficiency of a target gene in a *Bifidobacterium* sp., a promoter with a strong activity was isolated from a *Bifidobacterium* sp. GE65.

As for the *Bifidobacterium* strain containing a promoter with a strong activity, *Bifidobacterium* sp. GE65, *B. longum* MG1, *B. adolescentis* INT57, and *B. longum* ATCC15707 are preferable. The invention isolated a promoter having a nucleotide sequence represented by SEQ ID NO: 4 or SEQ ID NO: 5, from the *Bifidobacterium* sp. GE65.

Method for screening *Bifidobacterium* promoters may be according to a commonly known method in the art. Specially, the invention used a gfp gene, the gene having been used as a reporter gene.

First, a promoter probe vector, which binds to the promoters, was constructed. Using the promoter probe vector, vectors pbifGFP1, 2, 4, 5, 6, 7 and 10, in which the promoters expressing GFP in *E. coli* DH5α were inserted, were respectively isolated from *Bifidobacterium* sp. GE65. Among the vectors thus isolated, the vectors containing a relatively strong promoter, that is, pbifGFP7 that contains $P_G7$ promoter having a nucleotide sequence represented by SEQ ID NO: 4 and pbifGFP10 that contains $P_G10$ promoter having a nucleotide sequence represented by SEQ ID NO: 5 were obtained. FIG. 4 schematically illustrates a construction process of the promoter probe vector, and a cleavage map of the vector pbifGFP7 or pbifGFP10. GFP expression in *E. coli* was examined to select *E. coli* strains containing pbifGFP7 or pbifGFP10, yielding green fluorescence under UV irradiation. Specially, the vector pbifGFP7 or pbifGFP10 and the shuttle vector pBES2 according to the invention are recombined to construct pYBGFP7 or pYBGFP10. The vector pYBGFP7 or pYBGFP10 can express an amylase gene as a target gene under the promoter $P_G7$ or $P_G10$ according to the invention. FIG. 5 schematically illustrates a cleavage map of the recombinant vector pYBGFP7 or pYBGFP10.

As described above, the inventors constructed a recombinant vector by inserting a target gene into a shuttle vector which is replicated in both *E. coli* and *Bifidobacterium* sp., and expressed the recombinant protein in *Bifidobacterium* sp. The protein expressed from the target gene of the recombinant vector in *Bifidobacterium* sp. can be directly applied in preparing food additives and oral vaccines without additional purification process. On the other hand, conventional shuttle vectors which is replicated in both *E. coli* and *Bifidobacterium* sp. have been used to transform *Bifidobacterium* sp., expressing a target gene. However, such vectors have low transformation efficiency and poor expression for the target gene. The vector according to the invention expresses amylase with high efficiency, thus solving the above problems. The high level of gene expression was confirmed based on starch degradation by the transformant, *B. longum* MG1. The host cell for transformation was a strain of *B. longum* MG1 from which pMG1 was isolated, pMG1 having been used in constructing the shuttle vector pBES2, and further constructing the recombinant vector pYBamy59.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
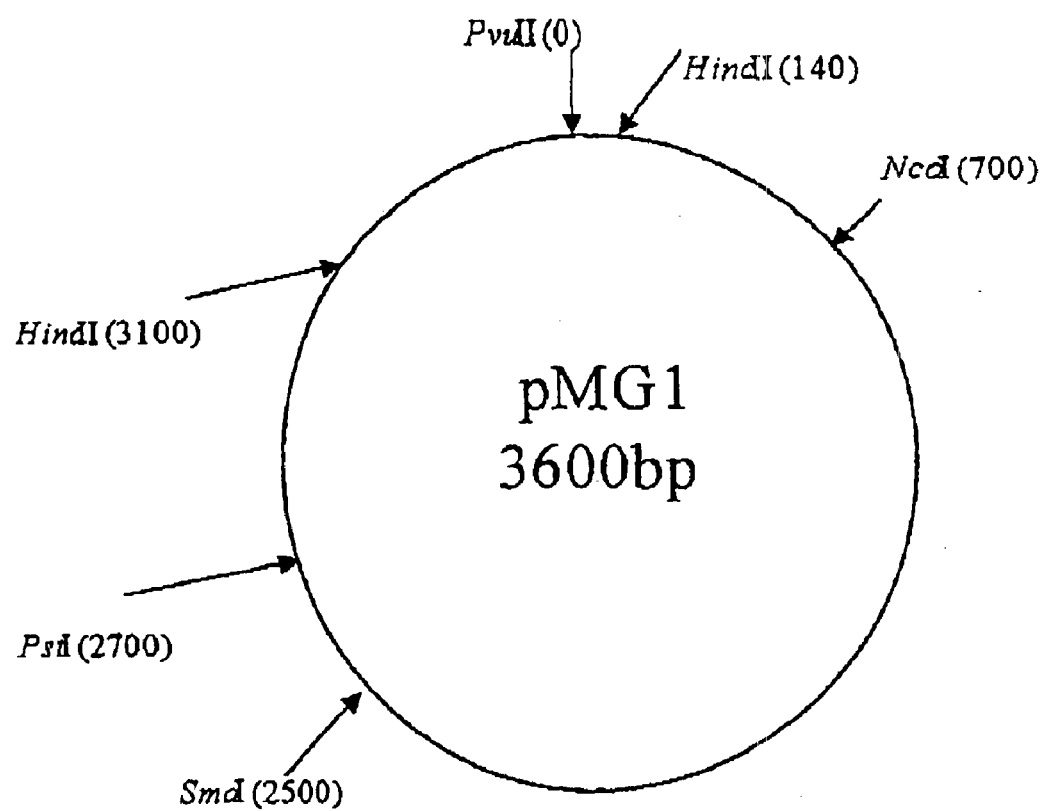
FIG. 1 schematically illustrates a cleavage map of pMG1 isolated from the *B. longum* MG1.

Hereinafter, the present invention will be described in detail, in conjunction with various examples.

These examples are provided only for illustrative purposes, and the present invention is not to be construed as being limited to those examples.

EXAMPLE 1

Isolation and Culture of *B. longum* MG1

To isolate a novel *Bifidobacterium* strain inhabiting the large intestine of Korean people, the inventors used a TP medium which had been developed by the present inventors (Korea Pat. Application No. 135,780). The TP medium consists of 10 g trypicase, 3.5 g proteose peptone No.3, 3 g ammonium sulfate, 2 g $KH_2PO_4$, 1 g $K_2HPO_4$, 0.5 g Cysteine.HCl(L-cysteine.HCl.$H_2O$), 0.2 g $MgSO_4$, 15 g agar, 50 ml transgalactooligosaccharide and 50 ml 30% sodium propionate. The medium was adjusted to pH 7.0 prior to use.

The feces were diluted to $10^{-8}$ to $10^{-9}$-fold with a diluent of 0.85% NaCl, and smeared on the TP medium, then cultured in an anaerobic incubator (DIFCO) at 37° C. for 48 hrs. After culturing, single colonies were isolated. The single colonies were subject to a morphological analysis using a microscope. Gram staining and an analysis of F6PPK, the enzyme unique to *Bifidobacteria*, were performed to identify the isolated target strain. The results showed that the bacteria are morphologically claviform and Y-shaped. In Gram staining, they were revealed to be Gram positive. They also exhibited the F6PPK activity, demonstrating *Bifidus* strains. Further, among the strains isolated, only strain containing plasmid were selected. Using sequence analysis of 16S rDNA genes, a *Bifidobacterium longum* MG1 strain was finally identified.

The strain thus isolated and identified was stored and cultured using BHI or MRS media containing 0.05% Cysteine.HCl (L-cysteine.HCl.$H_2O$). The BHI medium consists of 37 g BHI (Difco), 0.01 g Hemin, 0.05 g Cysteine.HCl, 0.001 g resazurin, and 0.001 g vitamin K. The MRS medium consists of 18.5 g glucose, 10 g pancreatin-digested gelatin, 8 g beef extract, 4 g yeast extract, 3 g sodium acetate, 2 g $K_2HPO_4$, 2 g ammonium citrate, 1 g Polysorbate 80, 0.2 g $MgSO_4$, 0.05 g MnSO4 and 0.5 g Cysteine.HCl.

EXAMPLE 2

Isolation of pMG1 from *B. logum* MG1 and Genetic Structural Analysis Thereof 2-1; Isolation of pMG1 from *B. longum* MG1

From the strain *B. longum* MG1 isolated and identified as in Example 1, a plasmid pMG1 represented by SEQ ID NO:

1 was isolated, according to Park et al. (Park, M. S. et al., *Letters in Applied Microbiology*, 25:5–7, 1997).

First, *B. longum* MG1 was cultured anaerobically at 37° C. in 15–20 ml MRS medium containing 0.05% Cysteine-.HCl. After centrifuging, the bacteria were collected. The bacteria were resuspended and washed twice with a TES solution (pH 8.0) consisting of 30 mM Tris.HCl, 50 mM NaCl and 5 mM EDTA. The supernatant was discarded. The bacteria pellet was added with 200 μl of sucrose solution (pH 8.0) which comprises 50 mM Tris. HCl, 1 mM EDTA and 5% sucrose containing 40 mg/ml lysozyme, followed by incubation at 37° C. for 1 hr. To this, a 400 μl alkaline SDS solution comprising 3% SDS and 0.2 N NaOH was added and immediately centrifuged at 15,000 rpm for 15 min. The supernatant was transferred to a new tube and mixed well with 650 μl isopropanol. Then, the sample was centrifuged at 15,000 rpm for 15 min, and the supernatant was removed. The resultant was dissolved in 320 μl sterile water. To this 7.5 M ammonium acetate containing 200 μl, of 0.5 mg/ml EtBr and with 350 μl phenol/chloroform were added. After vortexing, the supernatant was transferred to a new tube. The resulting sample was purified by precipitating with ethanol.

2-2: Genetic Structural Analysis of pMG1 of *B. longum* MG1

The plasmid pMG1 isolated as in Example 2-1 was digested with restriction enzymes *PvuII, HincII, PstI, NcoI* and *SmaI* to generate the pMG1 cleavage map. The results are shown in FIG. 1.

Also, the entire nucleotide sequence of pMG1 was determined. First, pMG1 was digested with *PiruII* and inserted into the *HincII* site in pUC19 (Clontech), which is used as a cloning vector in *E.coli*, constructing a plasmid vector pBES1. The plasmid pBES1 was treated with exonuclease III, thus obtaining nucleotide sequences having a deletion mutation. Respective nucleotide sequences of the plasmid thus obtained were subject to sequencing according to known methods, thereby determining the entire nucleotide sequence of pMG 1.

The results showed that pMG1 is 3,682 bp long with a G+C content of 65.1%. Sequence analysis using DNASIS (Hitachi) revealed that the plasmid contains several ORFs that are expected to be expressed. Among those ORFS, two distinct sequences which share high homology at their amino acid levels with other proteins were named ORF I and ORF II, respectively. ORF I has a mol cular weight of 29,000 Da and shows high homology with replication proteins of variable Gram-negative or Gram-positive bacteria. In addition, ORF I comprises nucleotide sequences known as iteron in which a 22 bp unit is repeated 4 times upstream of ORF I. On the other hand, ORF II has a molecular weight of 71,000 Da and shows high homology with mobilization proteins of other bacteria There is a nucleotide sequence of ori-T located upstream of the ORF II, which is presumed to play an important role in bacterial conjugation. Further, intracellular expression of the ORF I and ORF II was examined using a RT-PCR. As a result, the reaction products were seen to be 750 bp and 600 bp, respectively.

Moreover, each ORF has an AGGA sequence located 10 to 15 bp upstream thereof, which is expected to be a ribosome-binding site. ORF I comprises iteron sequences in its genetic structure in which a nucleotide sequence of 22 bp appears repeatedly 4 times upstream thereof. It is known that such iteron sequences are involved in regulating replication of plasmids. Also it is known that the ori-T sequence consisting of 12 bp, located upstream of the ORF II is an origin at which plasmid transfer occurs via conjugation.

EXAMPLE 3

Construction of Shuttle Vector pBES2

Figure 2:
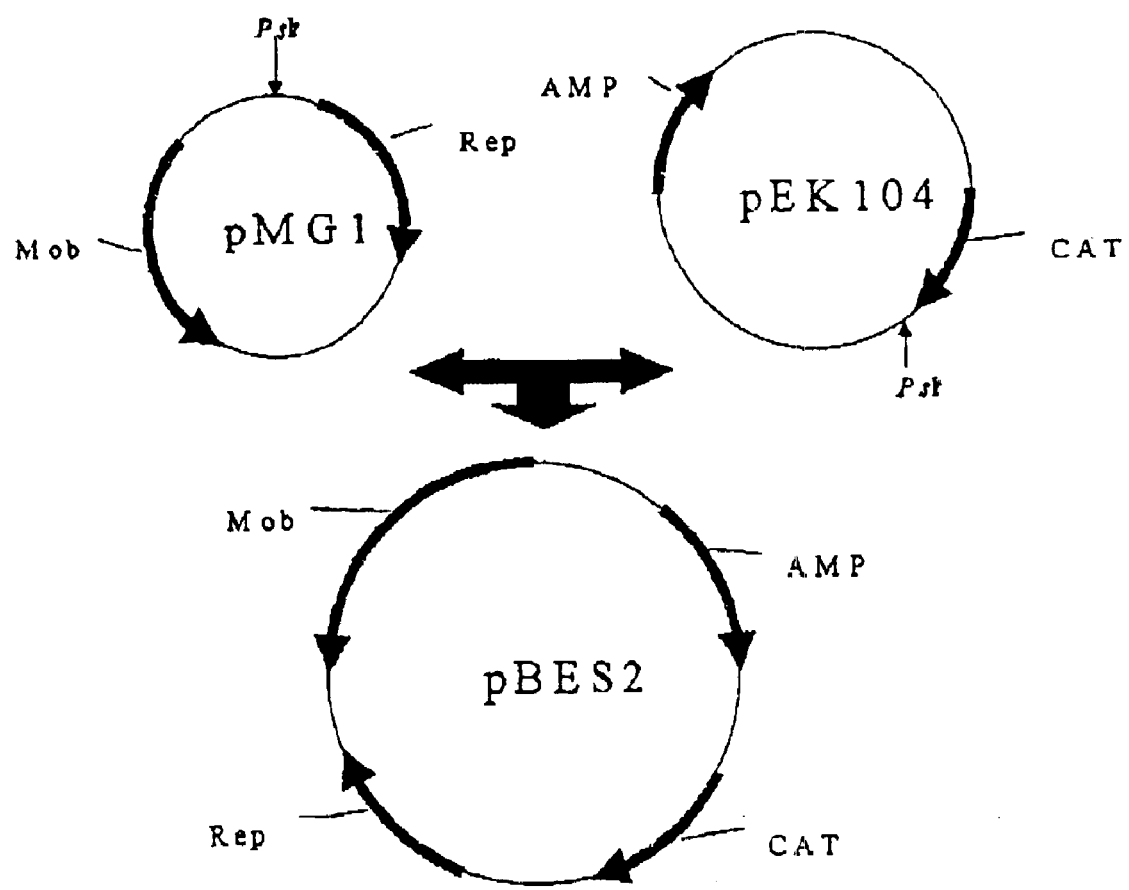
FIG. 2 illustrates a construction process of a shuttle vector pBES2 which is replicated in both *E. coli* and *Bifidobacterium* sp.
Figure 6:
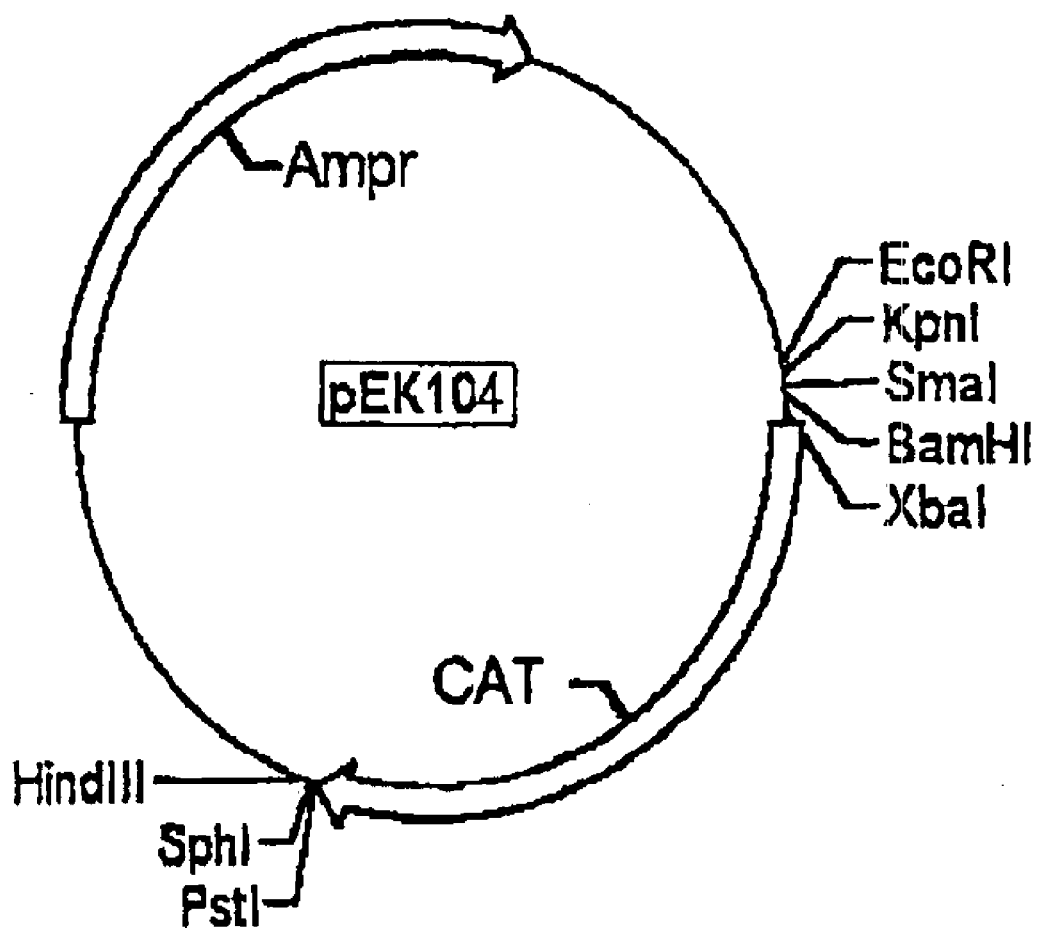
FIG. 6 schematically illustrates a cleavage map of a vector pEK104, being used in constructing a shuttle vector pBES2.

To construct a shuttle vector which is replicated in both *E. coli* and *Bifidobacterium* sp., pEK104, which is constructed by inserting a chloramphenicol acetyl transferase (CAT) gene derived from *Staphylococcus* sp. into pUC19, was first digested with Pst I, and ten ligated with the pMG1 prepared as in Example 2-1 which was digested with the same restriction enzyme, thus constructing a shuttle vector pBES2. A cleavage map of pEK104 is schematically illustrated in FIG. 6. As shown in FIG. 2, the shuttle vector pBES2 comprises a Mob gene having a nucleotide sequence represented by SEQ ID NO: 2, a Rep gene having a nucleotide sequence represented by SEQ ID NO: 3, an ampicillin resistance gene and a CAT gene. In the pBES2, the Mob gene and the Rep gene are ones derived from pMG1, while the ampicillin resistance gene and the CAT gene are ones derived from pEK104. The pBES2 has 7.8 kb in size. The shuttle vector showed high stability, maintaining its integrity within the cell even after 30 cycles of cell division.

EXAMPLE 4

Construction of Recombinant Vector and Expression Thereof

A recombinant vector was constructed by inserting a target gene into the shuttle vector pBES2 constructed as in Example 3, followed by performance of a transformation method using it, according to the present Example.

4-1: Construction of Recombinant Vector

Figure 3:
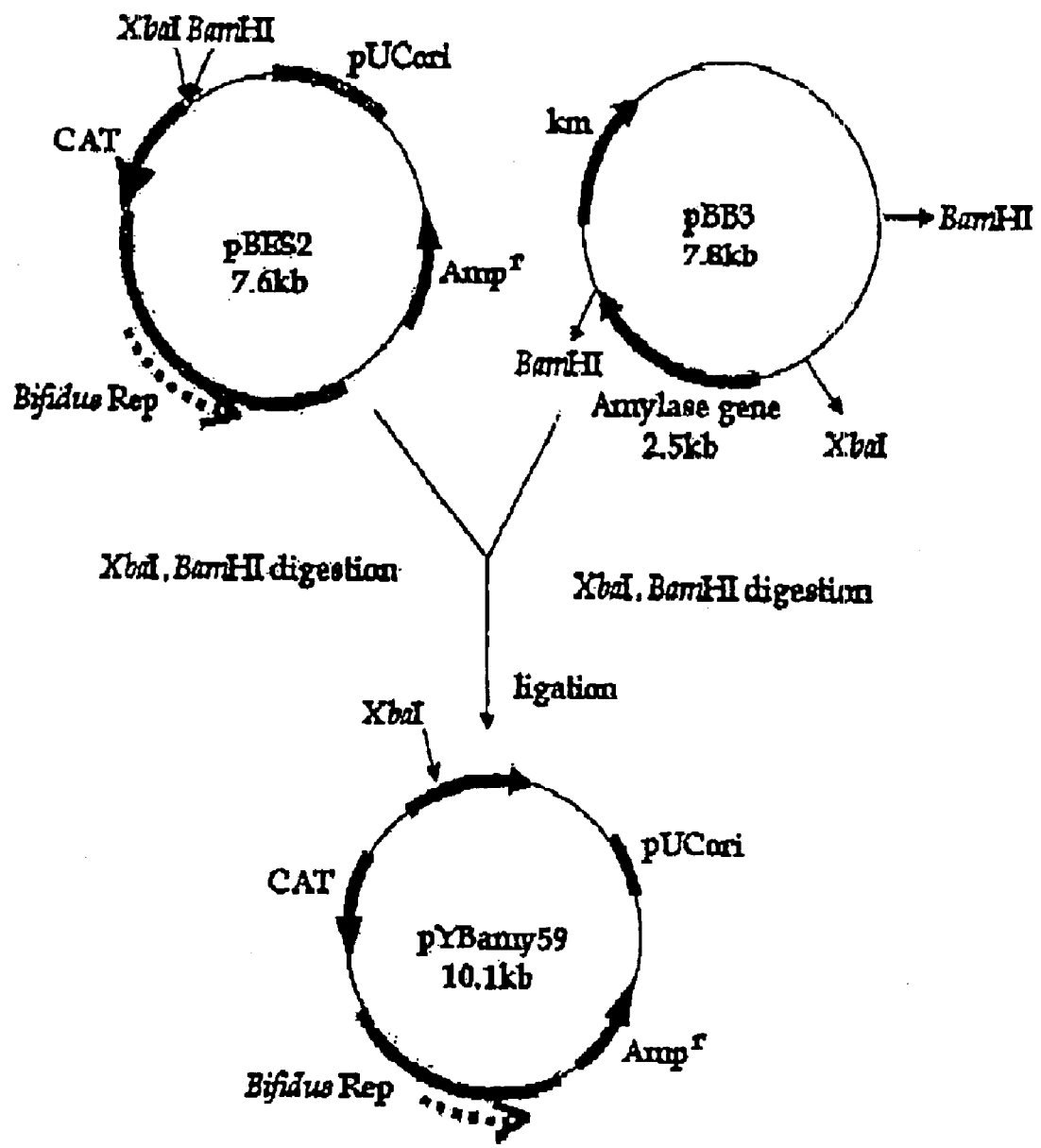
FIG. 3 illustrates a construction process of a recombinant vector pYBamy59 in which an amylase gene as a target gene is inserted into the shuttle vector pBES2 of FIG. 2.

To construct a recombinant vector which can be expressed in *B. longum* MG1, pBB3 carrying an amylase gene derived from *B. adolescentis* INT57 (disclosed by Sungyong Hong in Master's degree thesis, Korea Univ., Korea) was first digested with XbaI and BamHI. The digested vector was ligated with the shuttle vector pBES2 constructed as in Example 3, which was digested with the same restriction enzymes, thus constructing a recombinant vector pYBamy59. FIG. 3 schematically illustrates a cleavage map of the recombinant vector pYBamy59 and a construction process thereof. Using an electroporation method, *E. coli* DH5α was transformed with the recombinant vector. The transformant thus obtained was examined in terms of an activity of amylase which would be expressed therein. The transformant was smeared on a LB plate containing 1% starch and 20 μg/ml chloramphenicol and incubated at 37° C. for 24 hrs. The colonies on the plate were applied with Lugol's solution (0.5% $I_2$, 5% KI; w/v), and plaques around the colonies were detected, demonstrating the amylase activity. Further, the above transformant was cultured in LB medium, and pYBamy59 was isolated therefrom according to a known method for isolating plasmids. After aliquoting to a concentration of 1.0 to 1.5 μg/μl, the plasmid was used to transform the *Bifidobacterium* sp.

4-2: Transformation of *B. longum* MG1 Using Shuttle Vector

*B. longum* MG1 isolated as in Example 1 was inoculated into MRS medium containing 0.05% Cysteine.HCl and 0.5 M sucrose, followed by culturing at 37° C. overnight under an anaerobic condition. The preculture was inoculated into 250 ml of the same medium, and incubated until the absorbance at 600 nm reached 0.2. The culture was centrifuged at 6,000 rpm for 10 min at 4° C., and the bacteria were collected. The bacteria were resuspended in a cold 0.5 M sucrose solution. Such a step of centrifuging and resuspending was repeated twice, thus preparing competent cells.

The competent cells prepared as above were transformed with the shuttle vector pBES2 using electroporation. The transformation efficiency could be increased more than 10 times by treating with oxyrase.

4-3: Expression of Recombinant Vector

The competent cells of *B. longum* MG1 and *B. longum* KJ were transformed with pYBamy59 which was amplified in *E. coli* as in Example 4-1, using electroporation. The transformants were cultured in BHI medium containing 1% starch and 4 μg/ml chloramphenicol at 37° C. for 48 hrs. After culture, an amylase activity of the transformants was examined according to the same method as in Example 4-1. The results showed that the *Bifidobacterium* strains were transformed with the recombinant vector pYBamy59 constructed as in the invention. In addition to this, it could be seen that amylase is highly expressed in the *Bifidobacterium* strain.

EXAMPLE 5

Isolation of Promoter from *Bifidobacterium* sp. GE65 and Expression Thereof

To express a target gene in a *Bifidobacterium* sp. in an efficient manner, a promoter was isolated from *Bifidobacterium* sp. strain, and the expression level of the get gene was examined.

5-1; Isolation of Promoter from *Bifidobacterium* GE65

Figure 4:
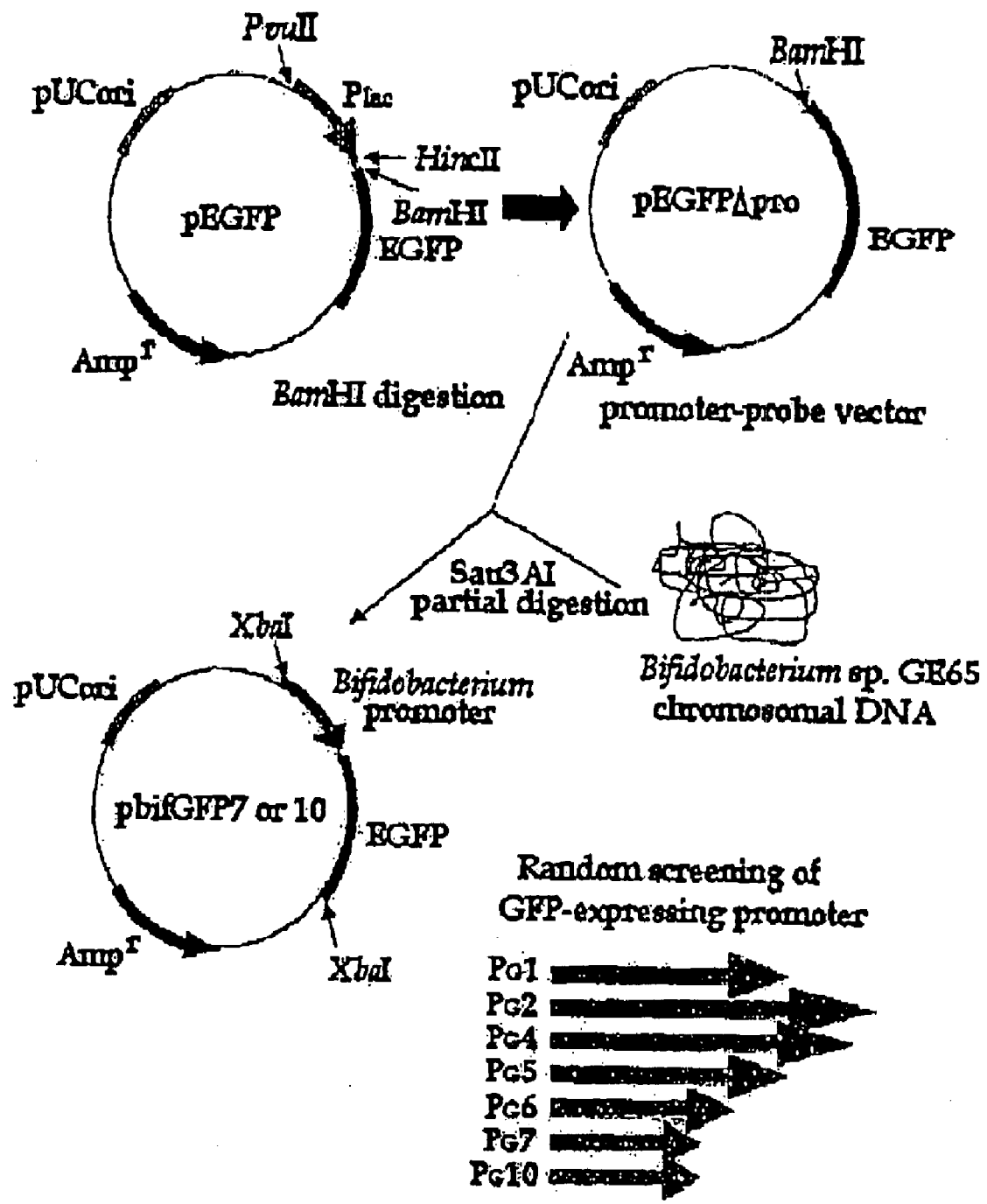
FIG. 4 illustrates a construction process of a vector pbifGFP7 or pbifGFP10 containing a promoter of *Bifidobacterium* sp. GE65, wherein the promoter have a nucleotide sequence represented by SEQ ID NO: 4 or SEQ ID NO: 5.

As a reporter gene, a gfp gene was used for screening a promoter of the *Bifidobacterium* sp. GE65. As shown in FIG. 4, $P_{lac}$ was removed from pEGFP (Clontech) by digesting with PvuII and HincII, thereby constructing a promoter probe vector, pEGFPΔpro The promoter probe vector was digested with BamHI, and ligated with a chromosomal DNA of *Bifidobacterium* sp. GE65 which was partially digested with Sau3AI. From the chromosomal DNA of *Bifidobacterium* sp. GE65 thus obtained, vectors pbifGFP1, 2, 4, 5, 6, 7, and 10, which can express GFP in *E. coli* DH5α were respectively isolated. Among the vectors thus isolated, the vectors containing a promoter with a relatively strong activity, pbifGFP7 and pbifGFP10 were obtained. In FIG. 4, $P_G1$, $P_G2$, $P_G4$, $P_G5$, $P_G6$, $P_G7$, and $P_G10$ represent promoters cloned into respective distinct pbifGFPs. Length of the arrows represents the length of each promoter. Especially, $P_G7$ having a nucleotide sequence represented by SEQ ID NO: 4 and $P_G10$ having a nucleotide sequence represented by SEQ ID NO: 5 are 228 bp and 224 bp long, respectively.

*E. coli* strains containing pbifGFP7 or pbifGFP10 were selected on the basis of GFP expression, yielding green fluorescence under UV irradiation.

5-2: Promoter Expression of *Bifidobacterium* sp. GE65

Figure 5:
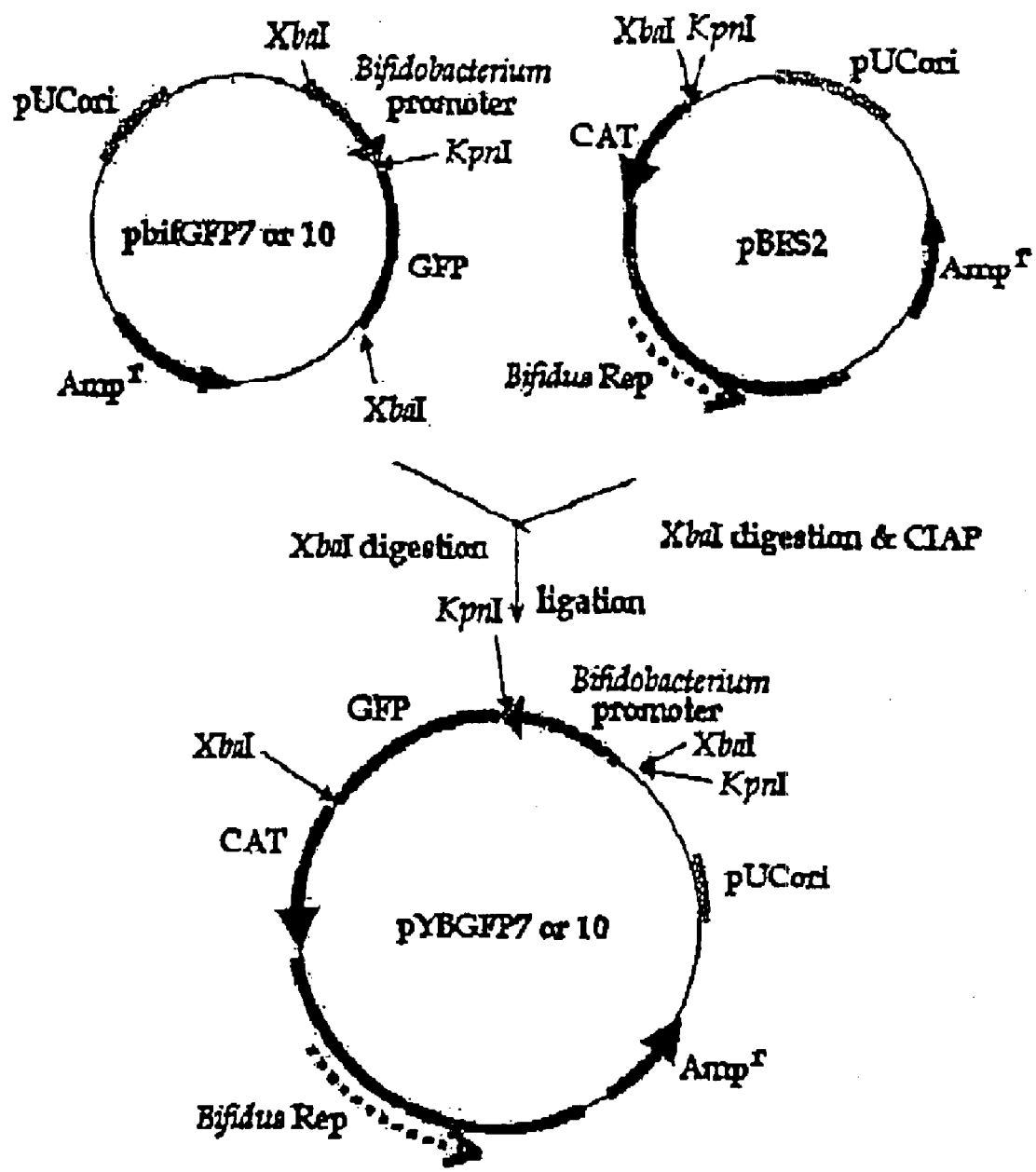
FIG. 5 illustrates a construction process of pYBGFP7 or pYBGFP10 in which a promoter and a GFP gene from the vector pbifGFP7 or pbifGFP10 of FIG. 4 is inserted into pBES2.

The shuttle vector pBES2 constructed in the invention was first digested with XbaI. The plasmid pbifGFP7 or pbifGFP10 isolated as in Example 5-1 was digested with the same restriction enzyme, obtaining the promoter $P_G7$ or $P_G10$. These $P_G7$ or $P_G10$ and the gfp gene were inserted into the digested vector pBES2, thus constructing a recombinant vector, pYBGFP7 or pYBGFP10. FIG. 5 schematically illustrates a cleavage map of the recombinant vector pYBGFP7 or pYBGFP10 and a construction process thereof. Using an electroporation method, *B. longum* MG1 was transformed with the recombinant vector pYBGFP7 or pYBGFP10. The transformant was smeared on an MRS plate and exposed to air for 48 hrs, followed by UV irradiation to detect green fluorescence by the GFP protein expression. In such a way, the promoter activity of the *Bifidobacterium* sp. isolated as in Example 51 could be seen. In addition, expression of the GFP protein was confirmed at a transcription level using RT-PCR (Sambrook, 1989), showing a 400 bp band corresponding to the gfp gene.

INDUSTRIAL APPLICABILITY

As apparent from the above description, the present inventors developed a shuttle vector which is replicated in both *E. coli* and *Bifidobacterium* sp. and expresses a target gene in an efficient manner. In addition, the inventors isolated a promoter which directs a strong expression of the target gene in *Bifidobacterium* sp. The shuttle vector and promoter of the invention can be used to express the target gene without the need for purification. Moreover, the target protein thus expressed in *Bifidobacterium* sp. is ready to use for addition to food products, offering advantages of the use thereof as a food additive and for preparing vaccines. In addition, with the development of such a shuttle vector, the potential for development of probiotics using *Bifidobacterium* sp. could be significantly increased.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A plasmid pMG1 having a nucleotide sequence represented by SEQ ID NO: 1.

2. A *Bifidobacterium longum* MG1 containing the plasmid of claim 1 (accession number: KCCM-10254).

3. A shuffle vector that is replicated in both *Bifidobacterium* sp. and *E. coli* and comprises a Mob gene having a nucleotide sequence represented by SEQ ID NO: 2, a Rep gene having a nucleotide sequence represented by SEQ ID NO: 3 and a selection marker.

4. The shuffle vector according to claim 3, wherein the shuffle vector is constructed by using the plasmid pMG1 of claim 1 and an *E. coli* vector for transformation.

5. The shuffle vector according to claim 4, wherein the vector for transformation is any one selected from the group consisting of pEK104, pUC19 and pBR322.

6. A shuttle vector pBES2 constructed by using the plasmid pMG1 of claim 1 and pEK104.

7. The shuffle vector according to claim 3, wherein the selection marker is at least one selected from the group consisting of an ampicillin resistance gene, a kanamycin resistance gene and a chloramphenicol acetyl transferas (CAT) gene.

8. A recombinant vector in which a heterologous gene is inserted into the shuttle vector of claim 3.

9. The recombinant vector according to claim 8, wherein the heterologous gene is any one selected from the group consisting of an amylase gene, a gene for vaccine, an gene for anticancer treatment and a gene exhibiting various physiological activities.

10. A recombinant vector pYBamy59 in which an amylase gene is inserted into the shuttle vector of claim 8.

11. A transformant transformed with the recombinant vector of claim 8.

12. A *Bifidobacterium longum* MG1 transformed with the recombinant vector pYBamy59 of claim 10 (accession number: KCCM-10255).

13. A transformation method comprising the steps of, (a) constructing a shuttle vector that is replicated in both *Bifidobacterium* sp. and *E. coli* using pMG1 of claim 1 and an *E. coli* plasmid;

(b) constructing a recombinant vector by inserting a heterologous gene into the shuttle vector; and (c) transforming the *Bifidobacterium* sp. used in the step (a) with the recombinant vector constructed in the step (b).

* * * * *

SEQUENCE LISTING

```
<160> NUMBER OF SEQ ID NOS: 5

<210> SEQ ID NO 1
<211> LENGTH: 3681
<212> TYPE: DNA
<213> ORGANISM: Bifidobacterium sp.

<400> SEQUENCE: 1
gcagatcaag tccctgcagg agaggcaggc ccagctcaag gcccgcgaga acgacctcat      60
ggcgcggcgc agggaacgcg aacgcagggc ccgcaccaag cgcctgatcg aggtcggcgc     120
gatggccgag tcggccgcgg gcttcgaggg cggcgacgag agggccaagg agcgcatagc     180
ccgcctcgtg cagctcggct cgctggtgga agccatgtgc tccaccgacg tgatggacaa     240
```

| | |
|---|---|
| ctacacgagc cgcgaggacc tcaagaccac cgtcaccaag gccctggaac acaacgtcag | 300 |
| aaccagcgat ggcatgaact ggaacctgca cgacctggtg tacgaggcgc tgagcgagga | 360 |
| atggggcaga agggacggcg agatcagcga cctctgggcg gacgacgggc aagcggata | 420 |
| ccagccaccc tcatacgagc cggtcaaccc cgaacgcagg actccccaaa caccctccga | 480 |
| tggcctgatc tgacgtccaa aaaaggcgc cgtgcgccct ttttaaatct tttaaaatct | 540 |
| ttttacattc ttttaggccc tccgcagccc ttggaaacat tgggctcaga ggatgttact | 600 |
| ggggacaaaa agggagcgaa ccggggacaa aagggagcg aaccggggac aaaagggag | 660 |
| cgaaccgggg acaaaaggg agcgaaccgg ggacgttgct aaaatgtgtc tcctttttga | 720 |
| tcaaggtggg gactcaaatt atttgtggac taacttaatt tgagtccccc ataggagcta | 780 |
| tgctaaggcc atgtccaatg agatcgtgaa gttcagcaac cagttcaaca acgtggcact | 840 |
| gaagaagttc gacgccgtgc acctggacgt gctcatggcg atcgcctcaa gggtgaggga | 900 |
| gaagggcacg gccacggtgg agttctcgtt cgaggagctg cgcggcctca tgcggctgag | 960 |
| gaagaacctg accaacaggc agctggccga caagatcgtg cagacgaacg cgcggctgct | 1020 |
| ggcgttgaac tacatgttcg aggattcggg caagatcatc cagttcgcgc tgttcacgaa | 1080 |
| gttcgttacc gacccgcagg aggcgaccct cgcggttggg gtcaacgagg agttcgcgtt | 1140 |
| cctgctcaac gacctgacca gccagttcac gcgcttcgag ctggccgagt tcgccgacct | 1200 |
| caaaagcaag tacgccaagg agttctaccg cagggccaaa caataccgca gctccggaat | 1260 |
| ctggaagatc agccgcgacg agttctgccg actgctcagc gttcccaaat ccacagccga | 1320 |
| gcaagtgaga gatctcaaca acgagtcct caagccgatt atcgaggagt gtgggccact | 1380 |
| ccttggactg aagatcgagc gccagtacgt gaaacgcagg ctgtcgggt tcgtgttcac | 1440 |
| gttcgcccgc gagacccctc cggtgatcga cgccaggccc gtggaggcga ggaaggcgga | 1500 |
| ggatgcgggc cattggacga agcgtcgccg ggtacgcga ggtgttcacg accactgagc | 1560 |
| tgttcgacgt gacggccgcg cgtgaccact tcgacggcac cgtggaggcc ggggaatgcc | 1620 |
| gtttctgcgc gtttgacgct cgcaaccgcg aacatcatgc gcagaacgcc ggaaagctgt | 1680 |
| tctagcggcc gtgtccgcgc cttggggcgg ttgcgcgctc catgggtcga tctgccgctg | 1740 |
| ttcgcgcctc ccgctggcct gtgagcctgt ccgtgcgctg tctgatctcg ttgagcaggt | 1800 |
| cggccttggt cctgggggcc tggcgtgatt cgaacgggct ggcctctccc cagtcctcgg | 1860 |
| gctcgctgag gtccagcggc tcgtcgccgg acggtgcggg ccgtttcgtg tcctgcgtcg | 1920 |
| ggttctccgc ctgcgcgcgt tgttcggcca tacgcagtgc gagggccttc acctgttcgg | 1980 |
| ggcttggccg ttcgctctcg gccgttcggc ctgttcgagc cgcctctcca gttcggccac | 2040 |
| gacgcctggt cctcggctgc atgtcgtggt cgtagatgcc cttggtggtc ctcatgcgga | 2100 |
| acctgttggc ctggtcccag tcggccggga tgtcggcgtc ttcgagccac ggcaccgccc | 2160 |
| cgcgcagcct ctcggactgc tctccggcca cctgctcggc gttccgcagc agcctgccgc | 2220 |
| gcttgaagat gttcgcgtcc ctggcctcgc gcgaggccgc ccgcgccacg tcgatgatct | 2280 |
| gcttggcggc ctcgtgctcc tcggtgcccg tggcttctcc accacttctc ccggttcccc | 2340 |
| acgtcggccc tcgcgtccat gagttttccg cggatcgcgg ccgtgtggtc ggccttgtcg | 2400 |
| gcttcgagct ggcggcgcgc gtcgccctcg aagtagcgcc agttcggctc ggccggttcc | 2460 |
| ggccgcgcct ggcgtcggcg cagccgcccg atcttggcgg cgaacagctc gcccaggcgg | 2520 |
| tcgaatatcc gtccgagttc ggcgcggacg gcggtcagca ggctgttgct gcgcctgatc | 2580 |
| tcacggtttgg tctggcacct ctcgctgacg cctccggccc gttcgatggc cctggcggcg | 2640 |

-continued

```
tatccctcgt ggatggtggg ttcgaggtcg ctgccctggt cttcgaggct cctgtggtcg    2700
attctcgcgg tctcgtccag ccgcgcgttg caggtgttcg cccaggactc gcgcagggcc    2760
ttgagcttgg ccttccggtc gagcgggttc agggacacgc tcgtgcgctt ccactgcctg    2820
cggccccgct tgtcggtctt ctgcctgccg gtctcggggt cgatcagcgg aacccgctcg    2880
ccccgctcgt ccagcacgta ctccatgcgc tgcttgagcc gggcccagcc gcccgtggcc    2940
gggtcgatct gccggttggc gacgaggatg tgcgcgtgcg ggttgttgcc ccgcccgtcg    3000
tcgtggatgg cgtaggtggc cgcgtagccg tccgcgttca ggttctcgcg gatgtactcc    3060
tccagcgcct gcacgcgctg cctgggggtg aactcgcgcg gcagggccac gacgatcttc    3120
ttggccggcc tcgccgtccg gccggtctcg tgcagctcga ccgcgttgaa cagcacggcg    3180
gggtcggcgt actcggccgg cgcgccctcc ggcagcaggg tgccgacgcg cagcacgtct    3240
cgctccttgc gcccgtagtc gtaggcgccg cgacgctcgt catgcacccg cctgccgctg    3300
atgtacgaga gcgtggccgt ggccttggaa ccgctcgcgc ggctcacgtt ggagacggac    3360
agatggtaga tcgccatcgg cttcggctcc tttcgtgatc ggcgcgggcg gcggggtgcg    3420
gggcctcggc cctgcggcaa ggggttccca ggggtgcggc gagcaccccc gggcctgccg    3480
ggaggctccc ccggaagggt gggaatccaa agggcaacgc ccgtggcccc cggagggcgc    3540
gcttacggaa aatgcaacct ccggttgcat gtaagtgcgc cctaatcttt gattagggat    3600
tccttgctgg tagaatcata tcaccatacg gatgatgcag accatgtaag gagccgtttc    3660
gatggtgaag agcctggatg a                                              3681
```

<210> SEQ ID NO 2
<211> LENGTH: 1941
<212> TYPE: DNA
<213> ORGANISM: Bifidobacterium sp.

<400> SEQUENCE: 2

```
atggcgatct accatctgtc cgtctccaac gtgagccgcg cgagcggttc caaggccacg      60
gccacgctct cgtacatcag cggcaggcgg gtgcatgacg agcgtcgcgg cgcctacgac     120
tacgggcgca aggagcgaga cgtgctgcgc gtcggcaccc tgctgccgga gggcgcgccg     180
gccgagtacg ccgaccccgc cgtgctgttc aacgcggtcg agctgacgga accggccgg      240
acggcgaggc cggccaagaa gatcgtcgtg gccctgccgc gcgagttcac ccccaggcag     300
cgcgtgcagg cgctggagga gtacatccgc gagaacctga acgcggacgg ctacgcggcc     360
acctacgcca tccacgacga cgggcggggc aacaacccgc acgcgcacat cctcgtcgcc     420
aaccggcaga tcgacccggc cacgggcggc tgggcccggc tcaagcagcg catggagtac     480
gtgctggacg agcggggcga gcgggttccg ctgatcgacc ccgagaccgg caggcagaag     540
accgacaagc gggggccgcag gcagtggaag cgcacgagcg tgtccctgaa cccgctcgac     600
cggaaggcca agctcaaggc cctgcgcgag tcctgggcga cacctgcaa cgcgcggctg      660
gacgagaccg cgagaatcga ccacaggagc ctcgaagacc agggcagcga cctcgaaccc     720
accatccacg agggatacgc cgccagggcc atcgaacggg ccggaggcgt cagcgagagg     780
tgccagacca accgtgagat caggcgcagc aacagcctgc tgaccgccgt ccgcgccgaa     840
ctcggacgga tattcgaccg cctgggcgag ctgttcgccg ccaagatcgg gcggctgcgc     900
cgacgcagg cgcggccgga accgccgag ccgaactggc gctacttcga gggcgacgcg     960
cgccgccagc tcgaagccga caaggccgac cacacggccg cgatccgcgg aaaactcatg    1020
```

```
gacgcgaggg ccgacgtggg gaaccgggag aagtggtgga gaagccacgg gcaccgagga    1080
gcacgaggcc gccaagcaga tcatcgacgt ggcgcgggcg gcctcgcgcg aggccaggga    1140
cgcgaacatc ttcaagcgcg gcaggctgct gcggaacgcc gagcaggtgg ccggagagca    1200
gtccgagagg ctgcgcgggg cggtgccgtg gctcgaagac gccgacatcc cggccgactg    1260
ggaccaggcc aacaggttcc gcatgaggac caccaaggcc atctacgacc acgacatgca    1320
gccgaggacc aggcgtcgtg gccgaactgg agaggcggct cgaacaggcc gaacggccga    1380
gagcgaacgg ccaagccccg aacaggtgaa ggccctcgca ctgcgtatgg ccgaacaacg    1440
cgcgcaggcg gagaacccga cgcaggacac gaaacggccc gcaccgtccg cgacgagcc     1500 gctggacctc agcgagcccg aggactgggg agaggccagc ccgttcgaat cacgccaggc    1560
ccccaggacc aaggccgacc tgctcaacga gatcagacag cgcacggaca ggctcacagg    1620
ccagcgggag gcgcgaacag cggcagatcg acccatggag cgcgcaaccg ccccaaggcg    1680
cggacacggc cgctagaaca gctttccggc gttctgcgca tgatgttcgc ggttgcgagc    1740
gtcaaacgcg cagaaacggc attccccggc ctccacggtg ccgtcgaagt ggtcacgcgc    1800
ggccgtcacg tcgaacagct cagtggtcgt gaacacctcg ccgtacccgg cgacgcttcg    1860
tccaatggcc cgcatcctcc gccttcctcg cctccacggg cctggcgtcg atcaccggag    1920
gggtctcgcg ggcgaacgtg a                                              1941

<210> SEQ ID NO 3
<211> LENGTH: 798
<212> TYPE: DNA
<213> ORGANISM: Bifidobacterium sp.

<400> SEQUENCE: 3
atgtccaatg agatcgtgaa gttcagcaac cagttcaaca acgtggcact gaagaagttc      60
gacgccgtgc acctggacgt gctcatggcg atcgcctcaa gggtgaggga aagggcacg     120 gccacggtgg agttctcgtt cgaggagctg cgcggcctca tgcggctgag gaagaacctg    180
accaacaggc agctggccga caagatcgtg cagacgaacg cgcggctgct ggcgttgaac    240
tacatgttcg aggattcggg caagatcatc cagttcgcgc tgttcacgaa gttcgttacc    300
gacccgcagg aggcgaccct cgcggttggg gtcaacgagg agttcgcgtt cctgctcaac    360
gacctgacca gccagttcac gcgcttcgag ctggccgagt tcgccgacct caaaagcaag    420
tacgccaagg agttctaccg cagggccaaa caataccgca gctccggaat ctggaagatc    480
agccgcgacg agttctgccg actgctcagc gttcccaaat ccacagccga gcaagtgaga    540
gatctcaaca aacgagtcct caagccgatt atcgaggagt gtgggccact ccttggactg    600
aagatcgagc gccagtacgt gaaacgcagg ctgtcggggt tcgtgttcac gttcgcccgc    660
gagacccctc cggtgatcga cgccaggccc gtggaggcga ggaaggcgga ggatgcgggc    720
cattggacga agcgtcgccg ggtacggcga ggtgttcacg accactgagc tgttcgacgt    780
gacggccgcg cgtgacca                                                  798

<210> SEQ ID NO 4
<211> LENGTH: 228
<212> TYPE: DNA
<213> ORGANISM: Bifidobacterium sp.

<400> SEQUENCE: 4
cagaaaattt caacttagct gattatctag ttcctacttt ggcttttatt cttgtactag     60
ttgtaatttt gctctttaaa gtcaactcag gacgtttcta taatcctttt gtataaaagt    120
```

```
ttcttttcct gccaagataa gttaaaatat actaataaaa agaaagaggg agagctttat        180
gaataacttt tcacaagaac cagaacgccg tacaattgtc gacgtaac                    228

<210> SEQ ID NO 5
<211> LENGTH: 224
<212> TYPE: DNA
<213> ORGANISM: Bifidobacterium sp.
<220> FEATURE:
<221> NAME/KEY: modified_base
<222> LOCATION: (31)
<223> OTHER INFORMATION: a, t, c, g, other or unknown
<220> FEATURE:
<221> NAME/KEY: modified_base
<222> LOCATION: (123)
<223> OTHER INFORMATION: a, t, c, g, other or unknown

<400> SEQUENCE: 5
cggggatcct ctagaggatc gtccacactt ncctgatgaa gtagcattag gagtaactta         60
caaagatgtt gccgatcact tagaaggtaa agatgtgagt gaagaagcag ctgaaccgat        120
tgnaaagttg tggaaaaaga gtgaacataa gcgtcatttg ccagtaacta tttttgatga       180
tttctataag caaaattagt taagtatttt tcttggagga aata                        224
```